United States Patent [19]

Kambara et al.

[11] Patent Number: 5,254,749
[45] Date of Patent: Oct. 19, 1993

[54] PROCESS FOR PRODUCING DIPENTAERYTHRITOL

[75] Inventors: Yoshihiko Kambara; Toru Idemoto; Yasuki Ono, all of Takaishi; Chika Tona, Sakai, all of Japan

[73] Assignee: Mitsui Toatsu Chemicals, Inc., Tokyo, Japan

[21] Appl. No.: 741,518
[22] PCT Filed: Jan. 8, 1991
[86] PCT No.: PCT/JP91/00004
§ 371 Date: Aug. 9, 1991
§ 102(e) Date: Aug. 9, 1991
[87] PCT Pub. No.: WO91/10633
PCT Pub. Date: Jul. 25, 1991

[30] Foreign Application Priority Data

Jan. 9, 1990 [JP] Japan ................................. 2-953
Sep. 26, 1990 [JP] Japan .............................. 2-254130
Oct. 8, 1990 [JP] Japan .............................. 2-268461

[51] Int. Cl.$^5$ .................... C07C 41/00; C07C 43/00
[52] U.S. Cl. ......................................... 568/698; 568/680
[58] Field of Search ............................... 568/680, 698

[56] References Cited

U.S. PATENT DOCUMENTS 2,462,047 2/1949 Wyler ................................. 568/698
2,820,066 1/1958 Taylor ................................ 568/680

*Primary Examiner*—Marianne M. Cintins
*Assistant Examiner*—Rebecca Cook
*Attorney, Agent, or Firm*—Oblon, Spivak, McClelland, Maier & Neustadt

[57] ABSTRACT

The present invention relates to a process for producing dipentaerythritol through the dehydration condensation of pentaerythritol in the presence of an acid catalyst. This production process comprises the step of carrying out the dehydration condensation preferably in the presence of an acid catalyst, and/or the step of lowering the temperature of the reaction mixture before the conversion of pentaerythritol becomes not less than 25%, to stop the reaction so that the concentration of tripentaerythritol formed during the reaction may not be increased, and at the same time to give a reaction mixture containing dipentaerythritol in an increased concentration.

12 Claims, No Drawings

PROCESS FOR PRODUCING DIPENTAERYTHRITOL

TECHNICAL FIELD

The present invention relates to a process for producing dipentaerythritol. More particularly it relates to a process for producing dipentaerythritol (hereinafter "D-PE") by dehydration condensation of pentaerythritol (hereinafter "PE") in the presence of an acid catalyst.

BACKGROUND ART

D-PE, for which demand is increasing as a starting material for, e.g., polyester, polyurethane, thermal stabilizers for polyvinyl chloride resins or lubricating oils, is a by-product obtained when PE is synthesized i.e., when PE is produced by reacting formaldehyde and acetaldehyde in the presence of an alkali. In conventional processes commonly used, this by-product is separated and purified to obtain the D-PE. In such processes, the following methods have been proposed in order to increase the rate of secondary formation of D-PE.

(1) A method in which the molar ratio of formaldehyde to acetaldehyde charged in a reaction system for the synthesis of PE is controlled to be smaller than 4, the theoretical molar ratio;

(2) a method in which the reaction is carried out using formaldehyde, acetaldehyde and an alkali agent in high concentrations; and (3) a method in which the reaction is carried out by adding and dissolving PE in an aqueous formaldehyde solution.

These methods, however, have had the disadvantages that PE and D-PE can be obtained in a low total yield and the main product PE has a poor quality. As an improved method of these methods:

(4) a method has been proposed in which the reaction is carried out by previously charging some amounts of formaldehyde, alkali and acetaldehyde in a reaction vessel and then simultaneously dropwise adding formaldehyde, alkali and acetaldehyde in amounts not less than their theoretical molar amounts while keeping reaction temperature at 50° C. or less (Japanese Patent Publication No. 1-44689).

Also known is (5) a method in which PE is subjected to dehydration condensation using phosphoric acid, sulfuric acid or the like to synthesize polypentaerythritol (U.S. Pat. No. 2,402,047).

Besides, also proposed as methods of separating D-PE from a mixture of PE and D-PE are:

(6) a method in which D-PE is crystallized from a D-PE/PE mixed solution prepared in a proportion of 30/70 or more (U.S. Pat. No. 2,448,566; and (7) a method in which D-PE is crystallized from a mixed solution having a PE/D-PE weight ratio of not more than 16 and a specific PE concentration (Japanese Patent Publication No. 2-10811).

However, the conventional method of producing D-PE by reacting acetaldehyde and formaldehyde [the above method (4)] has been involved in the problem that the purification step must be complicated in order to separate from PE and D-PE, by-product impurities such as sodium formate, bispentaerythritol monoformal (hereinafter "B-PE") and excess formaldehyde or an acetaldehyde-formaldehyde self-condensation product. It also has the problem that the production of D-PE can not overtake the increase in recent demand since the production possible for D-PE depends on the production of PE and is limited to 10 to 15% of the production of PE.

The method in which a polypentaerythritol mixture is synthesized from PE using phosphoric acid, sulfuric acid, an aromatic sulfonic acid or the like [the above (5)] aims at synthesis of various polypentaerythritol mixtures and hence does not clearly teach any means for selectively synthesizing D-PE. According to a finding of the present inventors, D-PE is firstly formed when PE is subjected to dehydration condensation using an acid catalyst, but the D-PE thus formed successively changes into tripentaerythritol (hereinafter "T-PE") and then into a high-molecular weight polypentaerythritol or intramolecular condensation product. Thus, the present inventors have found that this method is not practical as a process for producing D-PE.

The method disclosed in U.S. Pat. No. 2,448,566 [the above (6)] discloses a technique by which D-PE is separated from a mixture of PE and D-PE, and does not disclose the method of synthesizing D-PE in which the PE is subjected to self-condensation and the D-PE is obtained from the resulting reaction mixture. Accordingly, the method disclosed in this U.S. Patent has never been a method of producing D-PE independently of the manufacture of PE.

The method described in Japanese Patent Publication No. 2-10811 [the above (7)] has had, in addition to the same problems as in the above methods (1) to (4), the problem that it requires a troublesome step of adjusting PE concentration to a given range.

Objects of the present invention are to solve the above problems, and to provide a process of producing D-PE that can produce D-PE in a good efficiency, furthermore gives impurities in a low concentration, enables easy purification, and can obtain a high-quality product.

DISCLOSURE OF THE INVENTION

The present inventors made intensive studies in order to solve the above problems, and have reached an idea that, when the dehydration condensation of PE is carried out using an acid catalyst, the temperature of a reaction mixture is dropped to stop the reaction after formation of D-PE and before an excessive increase in the concentration of T-PE successively formed, and simultaneously to crystallize a part of the PE, thereby obtaining a reaction mixture in which D-PE has been concentrated to the desired concentration. Thus a first embodiment of the present invention has been accomplished.

Namely, the present invention provides a process for producing dipentaerythritol, comprising the steps of;

subjecting pentaerythritol to condensation in the state of a liquid phase at a temperature of from 200° C. to 260° C. in the presence of an acid catalyst;

lowering the temperature of the reaction mixture to crystallize a part of the pentaerythritol: and removing the crystallized pentaerythritol from the reaction mixture to give a reaction mixture containing dipentaerythritol in an increased concentration.

The present inventors have also discovered that the secondary formation of the impurities other than T-PE, produced when the dehydration condensation of PE is carried out using an acid catalyst in the liquid-phase molten state, can be remarkably decreased when the reaction is carried out in the presence of a polar solvent, and moreover it becomes easy to handle the reaction mixture. Based on this discovery, a second embodiment of the present invention has been accomplished.

Namely, the present invention provides a process for producing dipentaerythritol, comprising subjecting pentaerythritol to condensation in the state of a liquid phase in the presence of an acid catalyst; said condensation being carried out in the presence of a polar solvent.

BEST MODE FOR WORKING THE INVENTION

The first embodiment of the present invention will be described below in detail.

The acid catalyst used in the present invention refers to a substance usually used as a catalyst in dehydration condensation of alcohols. Examples thereof are set out in SHOKUBAI KOZA (Catalyst Course; Kodan-sha, published 1985), Vol. 8, page 278, Table 13-3. It includes, for example, mineral acids such as phosphoric acid, phosphorous acid and sulfuric acid, inorganic salts such as metal sulfates and metal phosphates, and clay minerals such as montmorillonite. Particularly preferred are phosphoric acid and metal phosphates. Metal species of the metal phosphates may include, for example, Al, B, Fe, Cr, Ti, Cu, Ni, Zn and Zr.

The optimum amount of the catalyst may vary depending on the type of the catalyst. In the case of phosphoric acid, for example, the catalyst may be in an amount of from 0.01 to 3.0 % by weight, preferably from 0.1 to 1.5% by weight, and more preferably from 0.3 to 1.0% by weight, based on the reaction mixture. An excessively small amount of the catalyst results in a small rate of reaction, and an excessively large amount thereof results in an increase in the secondary formation of impurities.

In the present invention, the PE is reacted in the state of a liquid phase. It is reacted, for example, in a liquid-phase molten state. In such an instance, the reaction temperature necessarily becomes higher than the melting point of the reaction mixture. Accordingly, it is suitable for the reaction to be carried out at a temperature of from 200° to 260° C., and preferably from 230° to 250° C. A reaction temperature lower than this range may undesirably make the reaction mixture begin to solidify and also result in a great lowering of the rate of reaction.

The acid catalyst causes the dehydration condensation of PE, so that D-PE is firstly formed. However, not only the D-PE is formed, but also T-PE is formed from the D-PE once formed and also polypentaerythritol with a higher molecular weight is consequently formed. It is basically difficult to completely prevent a series of these successive side reactions, but it is possible to prevent the side reactions to a certain extent.

More specifically, in order to prevent the side reactions, it is most effective to lower the concentration of D-PE in the reaction mixture. An excessively lowered concentration of D-PE, however, may result in a concurrent lowering of the yield itself of the D-PE.

Accordingly, in the present invention, the reaction mixture is cooled to lower its temperature to stop the reaction, before an increase in the concentration of the T-PE formed during the reaction. The present inventors have discovered that, in order to prevent an excessive increase in the concentration of T-PE in such an instance, the reaction should preferably be stopped before the conversion of PE comes to be 25% or more, and while the conversion is 2% or more, preferably from 5 to 22%, and more preferably from 8 to 18%. This discovery makes it possible to achieve both the secondary formation of impurities and the formation of the D-PE in a well-balanced state. The weight ratio of D-PE/PE in the reaction mixture at the time the conversion of PE is 25% may reasonably vary depending on the selectivity of reaction, the composition of the starting PE used, etc. In usual instances, it ranges approximately from 0.18 to 0.22.

The reaction time may greatly vary depending on the factors such as the type and mount of the catalyst used and the reaction temperature. It may range from 10 to 600 minutes, and preferably from 30 to 180 minutes, in approximation.

Herein the conversion is defined by the expression shown below.

$$\text{Conversion (\%)} = 100 - \frac{[\text{PE mole}] \text{ after reaction} \times 100}{[\text{PE mol} + 2 \times (\text{B-Pe mol})] \text{ before reaction}}$$

The reason why the conversion is defined based on the PE and B-PE as in the above is that the PE that is usually available through a commercial route usually contains about 3 to 6% of each of the D-PE and B-PE and hence a molecule of B-PE is presumed to form 2 molecules of PE and one molecule of formalin in the process of the present invention.

Incidentally, in the present invention, if the concentration of D-PE in the reaction mixture is lowered by controlling the conversion of PE to be preferably less than 25% in order to control the proportion of concentration of T-PE in the reaction mixture, it becomes difficult to directly separate and collect D-PE from the reaction mixture containing D-PE in such a low concentration, thereby bringing about an increase in the production cost of the D-PE.

Accordingly, in the present invention, the reaction is stopped by cooling and thereafter a part of unreacted PE is crystallized and removed from the reaction mixture, thereby increasing the concentration of D-PE in the solution. According to the present invention, the concentration of D-PE can be increased to from 5 to 30%, and preferably from 16 to 23% in approximation, when a part of PE in the reaction mixture is crystallized and removed from the reaction mixture having a D-PE concentration of from 3 to 25%, and preferably from 8 to 16%, in terms of weight ratio of D-PE/PEs (PEs refer to the total of PE, D-PE, T-PE and other reaction products). The amount of the PE removed after crystallization ranges from 5 to 35%, preferably from 10 to 30%, and more preferably from 23 to 28%, in approximation.

In the present invention, the crystallized PE may preferably be separated from the reaction mixture at a liquid temperature of about not higher than 195° C. in usual instances. The optimum temperature may vary depending on the composition of the reaction mixture, the type and amount of the catalyst used. It may preferably be in the range of from about 160° to 190° C., and more preferably from 176° to 188° C. This temperature range is in agreement with the temperature near the melting point of an eutectic composition of PE and D-PE (D-PE/PE=20/80).

In the present invention, as the step of cooling the reaction mixture and removing PE, the PE may be selectively crystallized and then the crystallized product may be removed. Alternatively, the reaction mixture is cooled to complete solidification, thereafter again heated to melt a part thereof, and then crystals of PE that remain at that time may be removed. In other words, the both are equivalent.

Any method known to those skilled in the art can be used as a method for solid-liquid separation to remove the crystallized PE from the reaction mixture and obtain the reaction mixture in which the D-PE has been concentrated. Usually the separation is carried out using a filter. There are no particular limitations on the type of the filter. It is preferred to use a sintered filter or a mesh filter made of a metal, taking account of the filtration carried out at a relatively high temperature.

There are no particular limitations on the types of reaction vessels. It is possible to use a stirring bath batch type, a pipe flow type, etc. For example, in the case when a reaction vessel of the stirring bath type, having a filter in the reaction vessel, there is an advantage that the PE in a solid phase remains in the reaction vessel after the solid-liquid separation and can be used for the subsequent reaction as it is.

According to the first embodiment of the present invention, a liquid solution in which the D-PE has been concentrated to about 19 to 21% by weight can be obtained when a reaction mixture having a PE conversion of about 14 to 18%, a D-PE concentration of about 9 to 13% by weight and a T-PE concentration of about 1 to 2% by weight is cooled to about 180° C. A commonly available separation means such as fractional crystallization may be applied to this liquid solution, so that D-PE with a high purity can be obtained. The unreacted PE may be again circulated to the reaction vessel and can be used as a starting material.

The second embodiment of the present invention will be described below.

As previously described, the present inventors have found out the problem that the impurities such as polypentaerythritol with a higher molecular weight than T-PE or intramolecular condensation products are secondarily formed in large quantities when the dehydration condensation of PE is carried out using an acid catalyst in a liquid-phase molten state. Although it is of course not completely clear why this arises, it can be for one thing presumed that the reaction temperature necessarily becomes higher than the melting point of the reaction mixture, in particular, comes to be 240° C. or higher at the initial stage of the reaction when the reaction is carried out in the liquid-phase molten state. In the first embodiment of the present invention, the present inventors have discovered that the step of filtering PE from the reaction mixture in which the concentration of D-PE has been increased is an operation for filtration at a temperature (about 160° to 190° C.) near the melting point of an eutectic composition of PE and D-PE (D-PE/PE=20/80). It is not necessarily easy to strictly control the temperatures during the operation for filtration at such a high temperature. It has been also found that the filter often clogs during the operation for filtration to bring about an insufficient concentration of D-PE. It has been still also found to be more preferable that the concentration of D-PE in the reaction mixture is controlled to be 20% or more by a simpler operation so that the yield of D-PE to be formed can be increased.

These new problems found out by the present inventors can be solved by carrying out the reaction in the presence of a polar solvent when the PE is subjected to condensation in the state of a liquid phase in the presence of an acid catalyst. That is to say, although nothing has been taken into account as to the use of a polar solvent in the reaction of this type, the present inventors have discovered that the use of a polar solvent brings about a decrease in the secondary formation of impurities in the reaction, makes it easy to operate the filtration of the reaction mixture in which the D-PE has been concentrated, and also facilitates well efficient progress of the concentration of D-PE.

The polar solvent used in the second embodiment of the present invention refers to a solvent comprised of a molecule having a dipole moment, which has a dielectric constant of from 15 to 100 at room temperature, and is stable under reaction conditions in which the acid catalyst is present. Such a polar solvent may be exemplified by dimethylformamide, dimethylsulfoxide. tributyl phosphate, sulfolane, 1,3-dimethyl-2-imidazolidinone, and water. In particular, sulfolane and 1 3-dimethyl-2-imidazolidinone can be preferably used because of their high boiling points and stability to acids. To be more surprising, the present inventors have discovered that water can be preferably used as the polar solvent not only in the reaction step but also in the subsequent step of concentrating the D-PE.

The polar solvent may be used in the condensation in an amount of from 5 to 70% by weight, and preferably from 10 to 30% by weight, based on the reaction mixture.

As the acid catalyst used here, the same one as used in the first embodiment of the present invention can be used. The optimum amount of the acid catalyst used may vary depending on the type of the catalyst. In the case of phosphoric acid, for example, the catalyst may be in an amount of from 0.01 to 3.0% by weight, and preferably from 0.1 to 2% by weight, based on the reaction mixture. An excessively small amount of the catalyst results in a small rate of reaction, and an excessively large amount thereof results in an increase in the secondary formation of impurities.

In the second embodiment of the present invention, the PE is reacted in the state of a liquid phase, and hence the PE may preferably be in a liquid phase in its entirety throughout the reaction. The reaction temperature is so set as to give such a state. The reaction temperature at which the PE is brought into a liquid phase in its entirety may vary depending on the type and amount of the solvent used. Taking account of the rate of reaction and the secondary formation of impurities, it is suitable for &he reaction to be carried out at a temperature of from 180° to 230° C., and preferably from 190° to 220° C. The reaction may also be carried out under application of a pressure.

In working the second embodiment of the present invention, it is preferred, like the first embodiment of the present invention, to provide the step of lowering the temperature of the reaction mixture to crystallize a part of the PE before an increase in the concentration of the T-PE formed during the reaction. In addition, it is also preferred to provide the step of removing the crystallized PE from the reaction mixture to give a reaction mixture containing D-PE in an increased concentration. The amount of the PE removed after crystallization may be determined according to the amount previously noted. Specifically stated, like the first embodiment of the present invention, the reaction temperature may be dropped before the conversion of PE comes to be 25% or more, to stop the reaction, and then the PE may be crystallized and removed. The reaction time may greatly vary depending on the factors such as the types and amounts of the solvent and catalyst used and the reaction temperature. It may range from 30 to 900 minutes, and preferably from 60 to 240 minutes, in approximation.

The temperature at which the PE is crystallized (i.e. solid-liquid separation temperature) may vary depending on the composition of the reaction mixture, the type and amount of the solvent used, the type and amount of the catalyst used etc. The temperature may range from about 40° to 160° C., and preferably from 50° to 155° C.

When the crystallized PE is removed by filtration, a polar solvent which is the same type as or a different type from the polar solvent used in the condensation may be further added to the reaction vessel so that the operability of filtration can be improved. When the polar solvent is additionally used, it is preferred to add it in such an amount that holds from 30 to 70% of the total weight of the reaction mixture.

According to the second embodiment of the present invention, a reaction mixture having a PE conversion of from 10 to 15% and a D-PE concentration (D-PE/PEs) of from 5 to 25% by weight, and preferably from 11 to 16% by weight, can be obtained from a starting material having 1 to 5%, in weight ratio, of D-PE/PEs (as previously described, PEs refer to the total of PE, D-PE, T-PE and other reaction products). From this reaction mixture, a liquid solution can be further obtained which has been concentrated to have a D-PE concentration (D-PE/PEs) of from 10 to 35% by weight, and preferably from 24 to 28% by weight, in approximation. A commonly available separation means such as fractional crystallization may be applied to this liquid solution, so that D-PE with a high purity can be readily obtained. The unreacted PE may be again circulated to the reaction vessel and can be used as a starting material.

The present invention will be described below in greater detail in the following Examples. The present invention is by no means limited to these Examples. In the following Examples, "%" used in the indication of liquid solution composition refers to "% by weight".

EXAMPLE 1

Into a reaction vessel made of stainless steel, having an internal volume of 1 lit and equipped with a thermometer, a heating-stirring device, and at its bottom a 5 $\mu$m mesh filter made of stainless steel and a liquid solution outlet, 500 g of a starting material PE was charged. This starting material was composed of 91.4% of PE, 3.8% of D-PE, 4.0% of B-PE and 0.2% of T-PE.

In an atmosphere of $N_2$, the temperature was raised to 240° C. so that the mixture was brought into a molten state, followed by addition of 1.5 g of 85% phosphoric acid to carry out reaction at 240° C. for 1 hour. After the reaction, a part of the reaction mixture was taken out and analyzed to reveal that it was composed of 79.7% of PE, 11.6% of D-PE, 1.6% of T-PE and 6.2% of other products, and no B-PE was detected. The results of this analysis show that the conversion of PE is 16.0% and the selectivity to D-PE is 55%.

Next, the temperature of the reaction mixture was lowered to 183° C. to crystallize a part of the unreacted PE, and the liquid phase portion was draw out through the filter at the bottom of the reaction vessel. As a result, 154 g of a liquid solution was obtained which was composed of 64.6% of PE, 19.6% of D-PE, 3.0% of T-PE and 11.7% of other products.

This liquid solution was cooled to crystallize the whole. Then, 330 g of water was added and the temperature was raised to 100° C. to dissolve the crystals. The solution was subsequently cooled to 42° C. to effect crystallization and the resulting crystals were collected by filtration. As a result, the weight of crystals excluding the water content was found to be 50.1 g, and D-PE, 53.1% (in weight ratio to PEs). To the resulting crystals, 110 g of water was added to again dissolve them, and the solution was cooled to 42° C. to effect crystallization. The resulting crystals were collected by filtration to give 27.8 g of crystals of D-PE with a high purity, composed of 84.2% of D-PE, 15.0% of T-PE and 0.7% of PE.

EXAMPLE 2

To 500 g of PE melted in the same manner as in Example 1, 20 g of zirconium phosphate was added and the reaction was carried out at 240° C. for 1 hour. As a result, a liquid solution was obtained which was composed of 78.5% of PE, 12.5% of D-PE, 1.8% of T-PE and 6.3% of other products. No B-PE was detected. The results of this analysis show that the conversion of PE is 17.6% and the selectivity to D-PE is 55.7%.

Next, the temperature of the reaction mixture was lowered to 188° C. to crystallize a part of the unreacted PE, and the liquid phase portion was draw out through the filter at the bottom of the reaction vessel. As a result, 160 g of a liquid solution was obtained which was composed of 63.8% of PE, 20.0% of D-PE, 3.3% of T-PE and 11.1% of other products.

Subsequently, the crystallization by cooling was operated twice by the use of water in the same manner as in Example 1, to give 28.0 g of crystals of D-PE with a high purity, composed of 84.0% of D-PE, 15.1% of T-PE and 0.8% of PE.

COMPARATIVE EXAMPLE 1

The reaction was carried out in the same manner as in Example 1 except that the reaction time was set to 2 hours. A reaction mixture was obtained which was composed of 64.5% of PE, 15.6% of D-PE, 6.4% of T-PE and 11.8% of other products. The results show that the conversion of PE is 32.3% and the selectivity to D-PE is 41.2%.

Next, the temperature of the reaction mixture was lowered to 180° C. to crystallize a part of the unreacted PE, and the liquid phase portion was draw out through the filter at the bottom of the reaction vessel. As a result, 176 g of a liquid solution was obtained which was composed of 46.0% of PE, 22.6% of D-PE, 10.8% of T-PE and 20.1% of other products.

Subsequently, the crystallization by cooling was operated twice by the use of water in the same manner as in Example 1, to give 46.0 g of crystals composed of 61.8% of D-PE, 35.0% of T-PE and 0.7% of PE. The resulting crystals were found to be crystals having a high T-PE content.

Thus, in the present Comparative Example, only crystals with a high T-PE content and a low-purity D-PE were obtainable when the reaction was carried out until the conversion of PE came to be 32.3%.

COMPARATIVE EXAMPLE 2

The reaction was carried out in the same manner as in Example 1 except that the reaction temperature was set to 265° C. and the reaction time to 30 minutes. A reaction mixture was obtained which was composed of 56.9% of PE, 14.9% of D-PE, 8.3% of T-PE and 18.5% of other products. The results show that the conversion of PE is 40.0% and the selectivity to D-PE is 31.2%.

Next, the temperature of the reaction mixture was lowered to 176° C. to crystallize a part of the unreacted PE, and the liquid phase portion was draw out through the filter at the bottom of the reaction vessel. As a result, 188 g of a liquid solution was obtained which was composed of 38.1% of PE, 20.1% of D-PE, 13.1% of T-PE and 28.3% of other products.

Subsequently, the crystallization by cooling was operated twice by the use of water in the same manner as in Example 1, to give 47.8 g of crystals composed of 55.6% of D-PE, 40.8% of T-PE and 0.7% of PE. The resulting crystals were found to be crystals having a high T-PE content like Comparative Example 1.

Thus, in the present Comparative Example, only crystals with a very high T-PE content and a low-purity D-PE were obtainable when the reaction was carried out until the conversion of PE came to be 40.0%.

EXAMPLE 3

The reaction was carried out in the same manner as in Example 1 except that the 85% phosphoric acid was used in an amount of 3 g, and the reaction temperature was firstly set to 240° C. to carry out the reaction for 15 minutes and thereafter lowered to 230° C. to carry out the reaction for 1 hour. As a result, a liquid solution was obtained which was composed of 80.7% of PE, 11.4% of D-PE, 1.3% of T-PE and 5.4% of other products. The results show that the conversion of PE is 14.8% and the selectivity to D-PE is 58.3%.

Next, the temperature of the reaction mixture was lowered to 188° C. to crystallize a part of the unreacted PE, and the liquid phase portion was draw out through the filter at the bottom of &he reaction vessel. As a result, 160 g of a liquid solution was obtained which was composed of 65.4% of PE, 19.5% of D-PE, 2.6% of T-PE and 11.4% of other products.

Subsequently, the crystallization by cooling was operated twice by the use of water in the same manner as in Example 1, to give 27.0 g of crystals of D-PE with a high purity, composed of 86.0% of D-PE, 13.1% of T-PE and 0.7% of PE.

EXAMPLE 4

The reaction was carried out in the same manner as in Example 1 except that titanium phosphate was used as the catalyst. As a result, a liquid solution was obtained which was composed of 82.9% of PE, 10.2% of D-PE, 1.1% of T-PE and 5.3% of other products. The results show that the conversion of PE is 13.0% and the selectivity to D-PE is 55.4%.

Next, the temperature of the reaction mixture was lowered to 188° C. to crystallize a part of the unreacted PE, and the liquid phase portion was draw out through the filter at the bottom of the reaction vessel. As a result, 145 g of a liquid solution was obtained which was composed of 65.1% of PE, 19.4% of D-PE, 2.5% of T-PE and 11.2% of other products.

Subsequently, the crystallization by cooling was operated twice by the use of water in the same manner as in Example 1, to give 22.9 g of crystals of D-PE with a high purity, composed of 85.8% of D-PE, 12.9% of T-PE and 1.0% of PE.

EXAMPLES 5 TO 7

The reaction was carried out in the same manner as in Example 2, using various catalysts. Results obtained are shown in Table 1.

TABLE 1

| Example | Catalyst | Kind of solution | PE | D-PE | T-PE | Others | D-PE/PE | *Amount (g) |
|---|---|---|---|---|---|---|---|---|
| 5 | Aluminum phosphate | (A): | 83.4 | 9.2 | 1.0 | 6.4 | 0.11 | |
| | | (B): | 66.1 | 19.7 | 2.1 | 12.1 | | 154 |
| 6 | Nickel phosphate | (A): | 82.2 | 9.8 | 0.9 | 7.1 | 0.12 | |
| | | (B): | 64.5 | 20.4 | 1.9 | 13.2 | | 162 |
| 7 | Chromium phosphate | (A): | 85.6 | 8.2 | 0.8 | 5.4 | 0.10 | |
| | | (B): | 66.4 | 19.6 | 1.9 | 12.1 | | 168 |

*Amount of draw-out liquid solution
(A): Reaction mixture
(B): Draw-out liquid solution

EXAMPLE 8

Into a reaction vessel made of stainless steel, having an internal volume of 1 lit and equipped with a thermometer, a pressure gauge, a heating-stirring device, and at its bottom a 5 μm mesh filter made of stainless steel and a liquid solution outlet, 400 g of a starting material PE and 100 g of water were charged. This starting material was composed of 91.4% of PE, 3.8% of D-PE, 4.0% of B-PE and 0.2% of T-PE.

In an atmosphere of $N_2$, the temperature was raised to 220° C. so that the mixture was brought into a molten state, followed by addition of 3.0 g of 85% phosphoric acid to carry out reaction at 220° C. for 1 hour. In the course of this reaction, the gauge indicated a pressure of 8 kg/cm$^2$G.

After the reaction, a part of the reaction mixture was taken out and analyzed to reveal that it was composed of 65.3% of PE, 10.1% of D-PE, 1.3% of T-PE and 2.7% of other products, and no B-PE was detected. The results of this analysis show that the conversion of PE is 13.8% and the selectivity to D-PE is 72.3%.

Next, 300 g of water was fed to the reaction vessel in 1 hour using a pump and also the temperature of the reaction mixture was lowered to 60° C. Thus a part of the unreacted PE was crystallized, and the liquid phase portion was draw out through the filter at the bottom of the reaction vessel. As a result, 518 g of a liquid solution was obtained which was composed of 18.7% of PE, 8.4% of D-PE, 0.9% of T-PE and 2.6% of other products. The proportion of D-PE/PEs was 28%.

This solution was cooled to 42° C. to cause deposition of crystals. Thereafter, the resulting crystals were collected by filtration. The resulting crystals were dissolved in 170 g of water, and the solution was cooled to 42° C. to effect re-crystallization, followed by collection by filtration. As a result, 34.5 g of crystals of D-PE with a high purity were obtained which were composed of 85.3% of D-PE, 13.4% of T-PE and 1.0% of PE.

EXAMPLE 9

The reaction was carried out in the same manner as in Example 8 except that& water was replaced with sulfolane. As a result, a liquid solution was obtained which was composed of 63.4% of PE, 10.8% of D-PE, 1.4% of T-PE and 3.4% of other products. No B-PE was detected. The results of this analysis show that the conversion of PE is 16.3% and the selectivity to D-PE is 67.2%.

Next, 300 g of sulfolane was fed to the reaction vessel in 1 hour using a pump and also the temperature of the reaction mixture was lowered to 150° C. Thus a part of the unreacted PE was crystallized, and the liquid phase portion was draw out through the filter at the bottom of the reaction vessel. As a result, 524 g of a liquid solution was obtained which was composed of 17.9% of PE, 8.7% of D-PE, 1.3% of T-PE and 3.4% of other products. The proportion of D-PE/PEs was 28%.

This liquid solution was cooled to room temperature to effect crystallization of PEs and the sulfolane was separated by filtration. As a result, 155 g of crystals were obtained.

Subsequently, the crystallization by cooling was operated twice by the use of water in the same manner as in Example 1, to give 38.0 g of crystals of D-PE with a high purity, composed of 84.9% of D-PE, 13.8% of T-PE and 0.9% of PE.

COMPARATIVE EXAMPLE 3

The reaction was carried out in the same manner as in Example 9 except that the reaction time was set to 200 minutes and the reaction temperature to 230° C. As a result, a reaction mixture was obtained which was composed of 52.2% of PE, 12.3% of D-PE, 5.0% of T-PE and 9.3% of other products. The results show that the conversion of PE is 31.1% and the selectivity to D-PE is 42.2%.

Next, the temperature of the reaction mixture was lowered to crystallize a part of the unreacted PE, and the liquid phase portion was draw out through the filter at the bottom of the reaction vessel. As a result, 552 g of a liquid solution was obtained which was composed of 14.0% of PE, 9.4% of D-PE, 4.3% of T-PE and 7.8% of other products. The proportion of D-PE/PEs was 26.4%.

In the same manner as in Example 9, the crystals of PEs were separated from sulfolane and thereafter the recrystallization was operated twice by the use of water. As a result, 53.7 g of crystals were obtained, composed of 62.0% of D-PE, 37.1% of T-PE and 0.7% of PE. The resulting crystals were found to be crystals having a high T-PE content.

Thus, in the present Comparative Example, only crystals with a high T-PE content and a low-purity D-PE were obtainable when the reaction was carried out until the conversion of PE came to be 31.1%.

EXAMPLE 10

The reaction was carried out in the same manner as in Example 8 except that 10 g of titanium phosphate was used as the catalyst in place of the phosphoric acid. As a result, a reaction mixture was obtained which was composed of 66.7% of PE, 9.2% of D-PE, 1.0% of T-PE and 2.4% of other products. No B-PE was detected. The results of this analysis show that &he conversion of PE is 12.5% and the selectivity to D-PE is 69.1%.

Next, 300 g of water was fed to the reaction vessel in 1 hour using a pump and also the temperature of the reaction mixture was lowered to 60° C. Thus a part of the unreacted PE was crystallized, and the liquid phase portion was draw out through the filter at the bottom of the reaction vessel. As a result, 483 g of a liquid solution was obtained which was composed of 19.7% of PE, 7.8% of D-PE, 1.0% of T-PE and 2.0% of other products. The proportion of D-PE/PEs was 25%.

Subsequently, the crystallization by cooling was operated twice by the use of water in the same manner as in Example 8, to give 30.7 g of crystals of D-PE with a high purity, composed of 85.5% of D-PE, 13.8% of T-PE and 0.9% of PE.

INDUSTRIAL UTILIZATION

The process for producing dipentaerythritol according to the present invention makes it possible to predominantly and well efficiently produce the dipentaerythritol itself, although it has been hitherto able to be produced only as secondary formation. The process also provide the dipentaerythritol in en industrial scale and at a low cost, that can be readily purified and has a high quality because of a low concentration of impurities formed after the synthesis reaction of the dipentaerythritol.

We claim:

1. A process for producing dipentaerythritol, comprising the steps of:
   condensing pentaerythritol in a liquid polar solvent in the presence of an acid catalyst to produce dipentaerithritol;
   lowering the temperature of the reaction mixture before the conversion of pentaerythritol reaches 25% to crystallize a part of pentaerythritol; and
   removing the crystallized pentaerythritol from the reaction mixture containing dipentaerythritol in an increased concentration.

2. A process according to claim 1, wherein the polar solvent has a dielectric constant with a value of from 15 to 100 at room temperature.

3. A process according to claim 2, wherein the polar solvent is dimethylformamide, dimethylsulfoxide, tributyl phosphate, sulfolane, 1,3-dimethyl-2-imidazolidinone, water or a mixture of any of these.

4. A process according to any of claims 1 to 3, wherein the polar solvent is present in an amount of from 5 to 70% based on the reaction mixture.

5. A process according to claim 1, wherein the temperature is lowered to a range of from 40° C. to 160° C.

6. A process according to claim 1, further comprising the step of separating dipentaerythritol from the reaction mixture containing dipentaerythritol in an increased concentration.

7. The process of claim 1, wherein said acid catalyst is selected from the group consisting of phosphoric acid, phosphorous acid, sulfuric acid, metal sulfates, metal phosphates and montmorillonite.

8. The process of claim 7, wherein said metal is selected from the group consisting of Al, B, Fe, Cr, Ti, Cu, Ni, Zn and Zr.

9. A process according to claim 3, wherein the polar solvent is sulfolane, 1,3-dimethyl-2-imidazolidinone, water or a mixture of any of these.

10. A process according to claim 9, wherein the polar solvent is sulfolane.

11. A process according to claim 9, wherein the polar solvent is 1,3-dimethyl-2-imidazolidinone.

12. A process according to claim 9, wherein the polar solvent is water.

* * * * *

UNITED STATES PATENT AND TRADEMARK OFFICE
CERTIFICATE OF CORRECTION

PATENT NO. : 5,254,749
DATED : October 19, 1993
INVENTOR(S) : Yoshihiko Kambara et al.

It is certified that error appears in the above-indentified patent and that said Letters Patent is hereby corrected as shown below:

On the title page, Item [75],

The third inventor's name, should read: --Yasuko Ono--

Signed and Sealed this

Fifth Day of April, 1994

*Attest:*

BRUCE LEHMAN

*Attesting Officer*     *Commissioner of Patents and Trademarks*